(12) United States Patent
Reed et al.

(10) Patent No.: US 8,294,092 B2
(45) Date of Patent: Oct. 23, 2012

(54) SYSTEM AND METHOD FOR TRAPPING AND MEASURING A CHARGED PARTICLE IN A LIQUID

(75) Inventors: Mark A. Reed, Monroe, CT (US);
Predrag S. Krstic, Knoxville, TN (US);
Weihua Guan, New Haven, CT (US);
Xiongce Zhao, Gaithersburg, MD (US)

(73) Assignees: Yale University, New Haven, CT (US);
UT-Battelle, LLC, Oak Ridge, TN (US);
University of Tennessee Research Foundation, Knoxville, TN (US)

(*) Notice: Subject to any disclaimer, the term of this patent is extended or adjusted under 35 U.S.C. 154(b) by 95 days.

(21) Appl. No.: 12/730,226

(22) Filed: Mar. 23, 2010

(65) Prior Publication Data

US 2011/0031389 A1 Feb. 10, 2011

Related U.S. Application Data

(60) Provisional application No. 61/162,374, filed on Mar. 23, 2009.

(51) Int. Cl.
*B01D 59/44* (2006.01)
(52) U.S. Cl. .................. 250/292; 250/288; 250/287
(58) Field of Classification Search .................. 250/292, 250/283, 287, 288
See application file for complete search history.

(56) References Cited

U.S. PATENT DOCUMENTS

| | | | |
|---|---|---|---|
| 2,939,592 A | 6/1960 | Paul et al. | |
| 5,248,883 A * | 9/1993 | Brewer et al. | 250/292 |
| 5,302,826 A * | 4/1994 | Wells | 250/292 |
| 5,650,617 A * | 7/1997 | Mordehai | 250/290 |
| 5,679,950 A * | 10/1997 | Baba et al. | 250/281 |
| 5,693,941 A * | 12/1997 | Barlow et al. | 250/292 |
| 5,783,824 A * | 7/1998 | Baba et al. | 250/281 |
| 5,994,697 A * | 11/1999 | Kato | 250/292 |
| 6,124,592 A * | 9/2000 | Spangler | 250/287 |
| 6,800,851 B1 * | 10/2004 | Zubarev et al. | 250/292 |
| 7,329,866 B2 * | 2/2008 | Wang | 250/290 |
| 7,807,963 B1 * | 10/2010 | Bier | 250/283 |
| 7,872,228 B1 * | 1/2011 | Kim et al. | 250/292 |
| 2005/0279932 A1 * | 12/2005 | Wang | 250/290 |
| 2006/0079002 A1 * | 4/2006 | Gologan et al. | 436/174 |
| 2009/0295372 A1 | 12/2009 | Krstic et al. | |
| 2010/0186524 A1 * | 7/2010 | Ariessohn et al. | 73/863.22 |
| 2011/0186724 A1 * | 8/2011 | Nolting et al. | 250/282 |
| 2011/0192969 A1 * | 8/2011 | Verentchikov | 250/282 |

OTHER PUBLICATIONS

Allison et al., 1996, "Cubic electrodynamic levitation trap with transparent electrodes", The Review of Scientific Instruments; 67(11):3806-3812.

(Continued)

*Primary Examiner* — Nikita Wells
*Assistant Examiner* — Johnnie L Smith
(74) *Attorney, Agent, or Firm* — Jones Day

(57) ABSTRACT

A system and method for trapping a charged particle is disclosed. A time-varying periodic multipole electric potential is generated in a trapping volume. A charged particle under the influence of the multipole electric field is confined to the trapping volume. A three electrode configuration giving rise to a 3D Paul trap and a four planar electrode configuration giving rise to a 2D Paul trap are disclosed.

19 Claims, 16 Drawing Sheets

OTHER PUBLICATIONS

Arnold et al., 1993, "Optimal long term imaging of a charged microparticle at the center of a Paul trap in an atmosphere near standard temperature and pressure: Experiment and stochastic model", Journal of Applied Physics; 74(7):4291-4297.

Arnott et al., 1998, "Rapid identification of comigrating gel-isolated proteins by ion trap-mass spectrometry", Electrophoresis; 19:968-980.

Blatt et al., 1986, "Brownian motion of a parametric oscillator: A model for ion confinement in radio frequency traps", Zeitschrift fur Physik D—Atoms, Molecules and Clusters; 4:121-126.

Brouard et al., 2001, "Brownian parametric oscillator: analytical results for a high-frequency driving field", Journal of Physics A: Mathematical and General; 34:11185-11191.

Cohen et al., 2005, "Method for trapping and manipulating nanoscale objects in solution", Applied Physics Letters; 86:1-3.

Cohen, 2005, "Control of nanoparticles with arbitrary two-dimensional force fields", Physical Review Letters; 94(11):118102-1-4.

Deng et al., 2007, "Brownian motion in a modulated optical trap", Journal of Optics A: Pure Applied Optics; 9:S256-S263.

Hasegawa et al., 1995, "Dynamics of a single particle in a Paul trap in the presence of the damping force", Applied Physics B; 61:159-163.

Hölzel et al., 2005, "Trapping single molecules by dielectrophoresis", Physical Review Letters; 95(12):128108-1-4.

Izmailov et al., 1994, "Parametrically driven microparticle in the presence of a stationary zero-mean stochastic source: Model for thermal equilibrium in the Paul trap", Physical Review E; 50(2):702-708.

Izmailov et al., 1995, "Microparticle driven by parametric and random forces: Theory and experiment", Physical Review E; 1325-1332.

Joseph et al., 2010, "A long DNA segment in a linear nanoscale Paul trap", Nanotechnology; 21:1-10.

Krstic et al., 2007, "Toward electronic conductance characterization of DNA nucleotide bases", Solid State Phenomena; 121-123:1387-1390.

Lagerqvist et al., 2006, "Fast DNA sequencing via transverse electronic transport", Nano Letters; 6(4):779-782.

NIH News, 2008, NHGRI seeks DNA sequencing technologies fit for routine laboratory and medical use, [online] U.S. Department of Health and Human Services National Institutes of Health; Aug. 20, 2008 [retrieved May 26, 2010]. Retrieved from the Internet: <URL:http://www.nih.gov/news/health/aug2008/nhgri-20.htm> pp. 1-4.

Oberacher et al., 2004, "Applicability of tandem mass spectrometry to the automated comparative sequencing of long-chain oligonucleotides", Journal of the American Society for Mass Spectrometry; 15:510-522.

Rosenthal et al., 2005, "Dielectrophoretic traps for single-particles patterning", Biophysical Journal; 88:2193-2205.

Tashiro et al., 2007, "Brownian motion under a time-dependent periodic potential proportional to the square of the position of a particle and classical fluctuation squeezing", Physica A; 377:401-411.

Winter et al., 1991, "Simple demonstration of storing macroscopic particles in a *Paul trap*", American Journal of Physics; 59(9):807-813.

Wuerker et al., 1959, "Electrodynamic containment of charged particles", Journal of Applied Physics; 30(3):342-349.

Zerbe et al., 1994, "Brownian parametric oscillators", Physical Review E; 49(5):3626-3635, with figures.

Zhang et al., 2006, "First-principles transversal DNA conductance deconstructed", Biophysical Journal; 91(1):L04-L06.

Zhao et al., 2008, "A molecular dynamics simulation study on trapping ions in a nanoscale Paul trap", Nanotechnology; 19:1-9.

Zikic et al., 2006, "Characterization of the tunneling conductance across DNA bases", Physical Review E; 011919:1-9.

Zwolak et al., 2007, "Physical approaches to DNA sequencing and detection", arXiv:0708.2724v1 [physics.bio-ph] [online], Physics Dept., California Institute of Technology, Pasadena, California; Aug. 20, 2007 [retrieved May 27, 2010]. Retrieved from the Internet: <URL: http://arxiv.org/PS_cache/arxiv/pdf/0708/0708.2724v1.pdf> pp. 1-26.

Zwolak, 2005, "Electronic signature of DNA nucleotides via transverse transport", Nano Letters; 5(3):421-424.

* cited by examiner

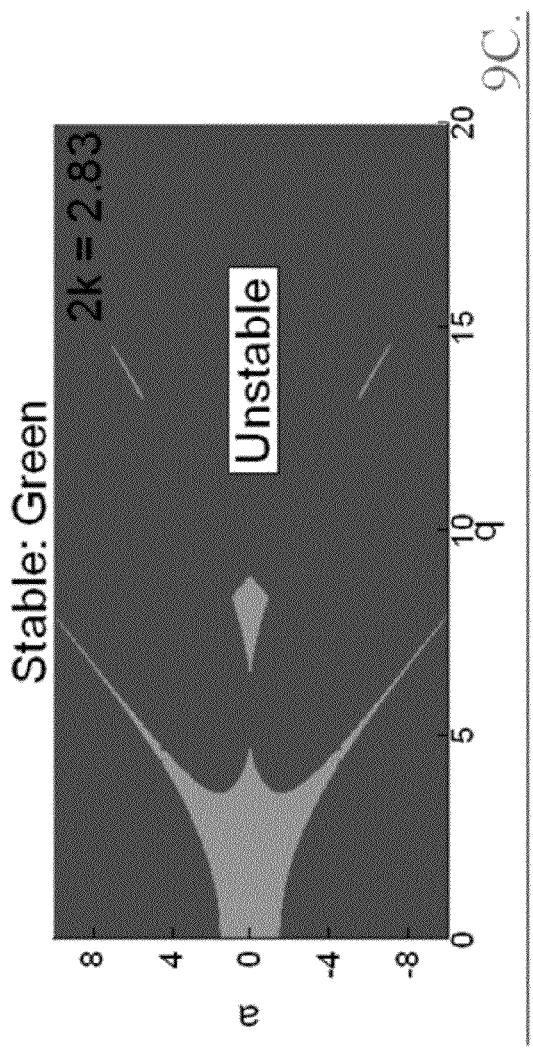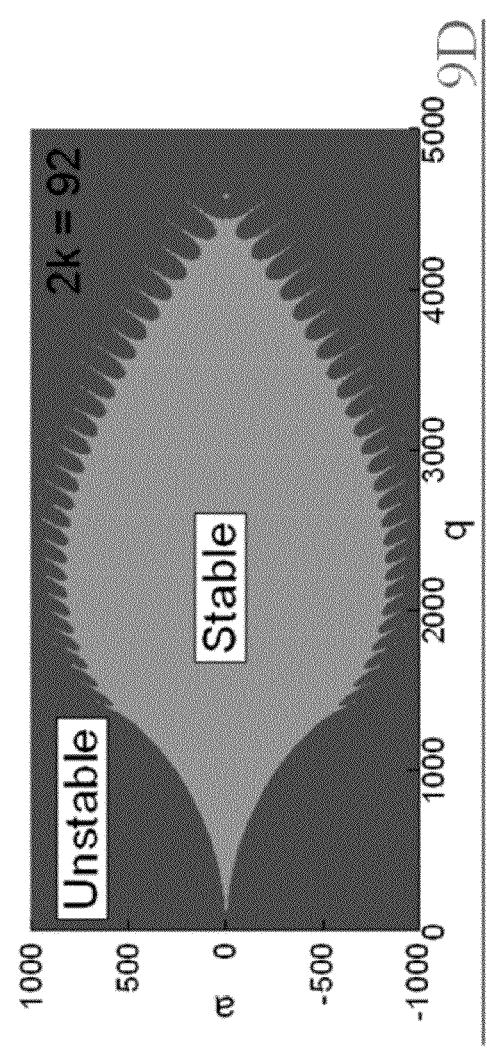
FIG. 9C
FIG. 9D

SYSTEM AND METHOD FOR TRAPPING AND MEASURING A CHARGED PARTICLE IN A LIQUID

CLAIM OF PRIORITY

This application claims the benefit of U.S. Provisional Patent Application No. 61/162,374 filed Mar. 23, 2009, the entire disclosure of which is incorporated by reference herein.

This invention was made with government support under Contract Number R21 HG003578 by the NIH National Human Genome Research Institute, R21 HG004764 by the NIH National Human Genome Research Institute, DE-AC05-00ER22725 by the U.S. Department of Energy, and DE-AC02-05CH11231 by the U.S. Department of Energy. The U.S. government has certain rights in this invention.

FIELD OF INVENTION

The present invention relates to systems and methods for trapping a charged particle in a liquid environment. Further, the present invention relates to systems and methods for controlling, sensing, and identifying trapped charged particles.

BACKGROUND

Nanoscale control of matter has led to enormous advances in many fields. In the biological and medical fields continued advances will allow for an unprecedented ability to examine and manipulate biological molecules and reactions. To achieve this, efficient methods for trapping, identifying, and sensing properties of biomolecules are needed.

One biomedical application in particular, genome sequencing, is a prime example of an application amenable to such a nanoscale approach. Current methods of genome sequencing such as chain-termination gel electrophoresis are slow and costly. This, coupled with the fact that a human genome contains approximately 3 billion base pairs makes sequencing even a single human genome a monumental task.

The possibility of direct genome sequencing using electronic measurements, wherein each base pair is identified as it basses by a nanoscale sensor, is potentially orders of magnitude faster and proportionally less costly then existing methods. These new techniques could enable sequencing of any individual's genome to prevent, diagnose, and treat diseases, potentially leading to a new genome-based medical practice.

One method of directly sequencing DNA involves translocating a fragment of Single-Stranded DNA (ssDNA) through a nanogap or a nanopore. These nanopores confine the DNA and allow for measurement of its properties as it translocates through the nanopore. Differences in the structure of the different nucleotides give rise to measurable effects which can be detected. Several measurements can distinguish between different bases, allowing for sequencing the DNA as it passes through the nanopore. If an ionic current is flowing through a nanopore, it has been found that DNA translocating through the pore masks the ionic current in a way specific to the nucleotide instantaneously passing through the pore. Alternatively, a bias applied across the transverse direction of the nucleotide can measure the capacitance or conductance of that specific nucleotide.

Repeatable measurements of the base specific signature of each nucleotide depends critically on its relative geometry during translocation. For example, it has been found that the variation in the transverse conductance due to the geometry of a base relative to an electrode can easily outweigh the differences between different types of nucleotides. Differences in the orientation and position of nucleotides relative to sensors must be minimized to make such a system feasible. Because an ssDNA is only about a nanometer wide, trapping methods that can achieve control on this scale are required. Further, DNA sequencing occurs in an aqueous or electrolytic environment, and an appropriate method of trapping the DNA must be compatible in such conditions. In a broader context, however, the general techniques of trapping and manipulating particles in liquid environment at a nanoscale resolution are important for a number of applications beyond DNA sequencing. Specifically, many molecules of interest become charged upon dissociation in an aqueous environment, and such a method could enable efficient trapping, sensing, identifying and sorting of these molecules.

Over the last few decades, a variety of manipulation techniques have been developed to achieve trapping of particles in liquids. These methods include optical tweezers, acoustic tweezers, and magnetic tweezers. These methods, however, can require complicated setups that have a low potential for integration into compact and cost effective devices. Because of this, increasing use has been made of electrical forces for achieving manipulations of particles in liquids.

Dielectrophoresis (DEP) forces arise from an object's polarizability. By applying a nonuniform electric field, it is possible to induce a dipole moment on an uncharged particle and create either an attractive or repulsive force. Using DEP it is possible to trap small particles in solutions. Indeed, the electrical trapping of objects in solution has so far been done primarily by DEP. DEP forces, however, are relatively weak, especially for smaller targets since the forces scale with the volume of the trapped object. Particles with diameters below 1 $\mu$m, for example, cannot be trapped by DEP as Brownian motion overwhelms the DEP forces. For this reason DEP based traps are not attractive for detection of very small biomolecules, such as ssDNA bases for direct sequencing.

Electrophoresis, in contrast, makes use of the interaction of an object's fixed charge and an electric field. Electrophoresis depends upon the amount of charge rather than polarizability, and is a first order interaction with the electrical field. While useful for moving particles, the multipole fields are unsuitable for trapping applications. This is because a charged particle cannot be stably held in a multipole electrostatic field due to the saddle shape of the potential that results from Laplace's equation. While a charged particle may be confined in one dimension, it will necessarily be unconfined in another. Although this would seem to preclude electrophoretic traps, one can get around this problem by using a time-varying field.

One such system is the anti-Brownian electrophoretic trap (ABEL) based on a feed-back mechanism. In this system the computer visually tracks the trajectory of a charged particle. Using this information, the computer calculates a feedback voltage which is applied to electrodes arranged around a trapping volume containing the target particle. The applied feedback voltage creates an force to counteract the particles motion and return it to the center of the trapping volume. This technique requires a visible target and stability depends upon a fast sampling rate. These limitations make the technique unsuitable for many applications.

There remains a need in the art for systems and methods for controlling charged particles in liquids. Preferably such a system would utilize the strong electrophoresis force without requiring complicated setups or detection schemes. Such a system is desirable as it could enable efficient control of biomolecules for a variety of applications including DNA sequencing.

In contrast to trapping techniques in a liquid environment, trapping charged particles in vacuum and gaseous environments using electromagnetism is a mature field. It is known that atomic ions and other charged particles can be confined by particular arrangements of electromagnetic fields in these environments. One such device is a Paul trap, which can be used to dynamically confine particles in vacuum or gas through spatially inhomogeneous and alternating radio frequency (RF) electrical fields. In this type of device a set of electrodes generates an alternating quadrupole potential which can provide confinement in two or three dimensions. While at any given moment the potential within the trap is an unstable saddle point, changing the orientation of this saddle point rapidly by providing an appropriate RF field can in fact create a dynamically stable trap.

Paul traps are used in vacuum and gaseous environments today for a number of applications including analytical chemistry and aerosol research, and their version, a linear Paul trap, is an important component of Mass Spectrometry instruments. While Paul traps exhibit many properties which are attractive as a potential trapping method for charged particles in liquids, it has been the general consensus that such a device was incompatible with a liquid environment. Polarization of the liquid, thermal fluctuations due to Brownian motion, charge screening, and viscosity were all effects indicated that such a device was impossible. To date, no Paul traps have been demonstrated in a liquid environment.

Accordingly, presently there is a need in the art for Paul traps capable of trapping charged particles in liquids. Additionally, there is a need for incorporating these novel Paul traps into systems for controlling, sensing, and identifying charged particles in a liquid environment.

SUMMARY OF THE INVENTION

A system for trapping a charged particle in a trapping volume is disclosed. The system comprises at least three confining electrodes distributed around the trapping volume. Between these three confining electrodes is a liquid container adapted to hold a liquid carrying the charged particle. A power source electrically connecting the at least three confining electrodes is capable of applying a time-varying periodic voltage bias between the at least three confining electrodes for creation of a time-varying periodic multipole electric potential in the trapping volume. The multipole electric potential is at least a quadrupole electric potential. The trapping volume may be microscopic or nanoscopic. The liquid container can be fluidly connected to a microfluidic channel for supplying liquid to the liquid container. The liquid container is adapted to hold a liquid solution comprising an electrolyte.

In some embodiments the three confining electrodes are N confining electrodes where N is an even whole number of four or greater. These N confining electrodes are positioned around the trapping volume so that the multipole electric potential in the trapping volume is orthogonal to a longitudinal axis to the trapping volume. These N confining electrodes may be coplanar in a plane orthogonal to the longitudinal axis of the trapping volume.

Two electrodes are arranged along the longitudinal axis of the trapping volume so that the trapping volume is between them. These two electrodes are electrically connected to a power source capable of applying a voltage bias for controlling the movement of the charged particle along the longitudinal axis of the trapping volume.

In another embodiment the system for trapping a charged particle comprises two longitudinally confining electrodes along a longitudinal axis. A transversely confining electrode encircles the region between the two longitudinally confining electrodes transversely to the longitudinal axis. A liquid container between the two longitudinally confining electrodes and the transversely confining electrode is adapted to hold a liquid carrying the charged particle. A power source is electrically connected to the longitudinally confining electrodes and the transversely confining electrode and is capable of applying a time-varying periodic voltage bias to create a time-varying quadrupole electric potential in the trapping volume.

A method of trapping a charged particle in a trapping volume is also disclosed. The method comprises: providing a liquid containing the charged particle; positioning the liquid containing the charged particle between at least three confining electrodes; applying a time-varying periodic voltage bias to the at least three confining electrodes distributed around the trapping volume; generating a multipole electric potential in the trapping volume, wherein the multipole electric potential is at least a quadrupole; and trapping the charged particle within the trapping volume.

In some embodiments of the method the at least three confining electrodes are N confining electrodes positioned around the trapping volume so that the multipole electric potential in the trapping volume is orthogonal to a longitudinal axis of the trapping volume, wherein N is an even whole number of four or greater. The N confining electrodes may also be coplanar in a plane orthogonal to the longitudinal axis of the trapping volume.

BRIEF DESCRIPTION OF THE DRAWINGS

FIG. 9C-9D illustrate the change in stability regions with fluids;

DETAILED DESCRIPTION OF THE EMBODIMENTS

Figure 1:
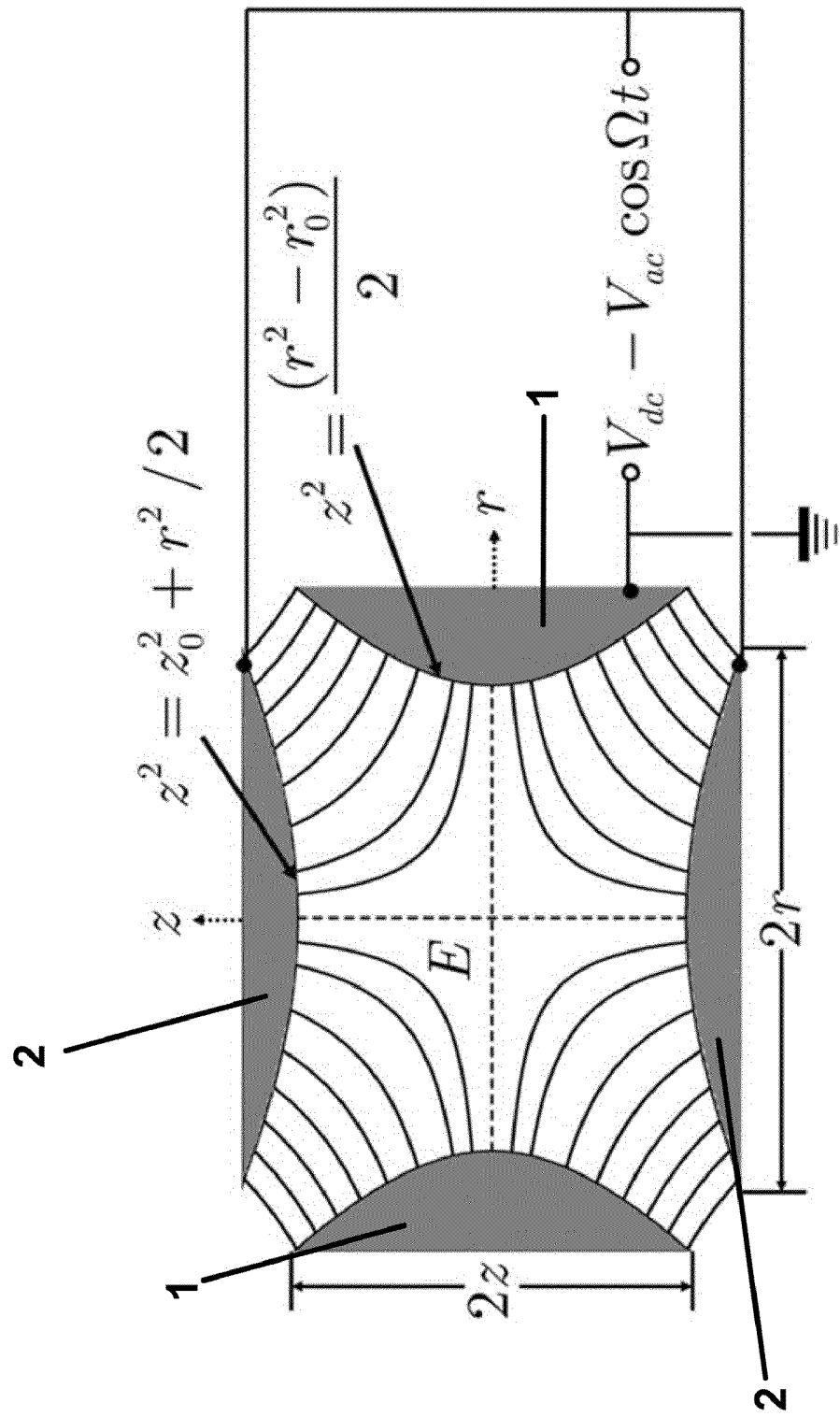
FIG. 1 illustrates a sectional view of a 3D Paul trap.

The present invention advantageously provides the ability to trap charged particles. The term "trapping" and its variations indicate that movement of the charged particle is restricted in at least one dimension. Trapping is accomplished by providing a particular form of alternating electric potential which causes the particle to become trapped within a narrow 2D or small 3D volume. This volume can be made narrow (2D) or small (3D) enough to confine and stabilize microscopic and nanoscopic charged particles. The term "nanoscopic" and its variations indicate that the particle is of nanoscale dimensions (nanosized), i.e., a dimension sufficiently small that the properties of an object of such dimensions are predominantly governed by the behavior of individual atoms. Typically, a nanoscopic or nanoscale object refers to an object having at least one dimension within a range of about 1 to 100 nanometers (nm). The term "microscopic" and its variations indicate that the particle is of the dimensions of a micron.

In some embodiments, the charged particle is suspended in a liquid environment. The liquid can be water or some other liquid such as glycerine. The liquid can also be a solvent. Electrolytes or other solutes may be present in the liquid.

The charged particle to be trapped can be any particle of appropriate size and mass that is charged, including ions, molecules, polymers, nano- and micro-sized clusters. In some embodiments, the charged particle is a biomolecule. A biomolecule is any molecule that is involved in a biological process or found in a living organism. The biomolecule can be, for example, a nucleobase-containing molecule. Some examples of nucleobases include the pyrimidines (e.g., cytosine, thymine, and uracil) and the purines (e.g., adenine and guanine) Some examples of nucleobase-containing molecules that can be trapped herein include oligonucleotides, and nucleic acid polymers. The oligonucleotides and nucleic acid polymers can be deoxyribonucleic acid (DNA)-based or ribonucleic acid (RNA)-based. The biomolecule can also be, for example, an amino acid-containing molecule. Some examples of amino acid-containing molecules include the amino acids, peptides, oligopeptides, and polypeptides (e.g., proteins, such as enzymes). In other embodiments, the charged particle may be an inorganic molecule such as Silicon Dioxide, Silicon Nitride, or any type of nano or micro particle which is charged or may become charged in solution. Finally, nano and micron-size clusters, often show charging properties at the interface of their surface exposed to a liquid and electrolyte.

A device which provides the alternating electric potential necessary for trapping a charged particle is called a Paul trap, which is a quadrupole type trap. Quadrupole trap types are those that lead to an electric potential F(x, y, z, t) of approximately quadrupolar spatial shape in the center. Their functionality emerges from the assumption that the particles are bound to an axis of the system if a binding force which acts on them increases linearly with their distance (F=−cr). Cylindrically symmetric electrical potential is ideally in the form of $$\Phi(r, z, t) = \frac{\Phi_0}{2r_0^2}(\alpha x^2 + \beta y^2 + \gamma z^2).$$

The condition that this potential has to fulfill the Laplace equation $\nabla \Phi_0 = 0$ at every instant in time leads to a constraint $\alpha + \beta + \gamma = 0$ of the three geometric factors, which can be achieved in various ways, thus defining various possible geometries and types of quadrupole traps. From this constraint it follows that local three-dimensional minimum the potential can only trap charges in a dynamical way. The driving frequency and voltages can be chosen in such a way that the time-dependent potential will give rise to a stable, approximately harmonic motion of the trapped particle, in all or chosen directions. This can easily be demonstrated by a mechanical analogue. The equipotential lines form a saddle surface in a trap. A small, still ball set on the saddle is not in a stable equilibrium and will roll down the saddle. But if one sets the saddle into rotation with an appropriate frequency the ball motion will become stable in form of small oscillations and can remain on the saddle for an extended time.

One of the most well known trap configurations is the 3D Paul trap, with $\alpha = \beta = 1$, $\gamma = -2$. This trap comprises ring-shaped metal electrode 1 and two cap-shaped metal electrodes 2, whose internal surfaces are defined as hyperbolic surfaces shown schematically in FIG. 1. The surfaces coincide with equipotential surfaces. Ring-shaped metal electrode 1 is half-way between the two cap-shaped metal electrodes 2, i.e. $r_0^2 = 2z_0^2$. The two cap-shaped metal electrodes 2 define a longitudinal axis between them along the z-direction. The ring-shaped metal electrode encircles this longitudinal axis in a plane transverse to the longitudinal axis.

During operation, the charged particle is trapped in the space between these three electrodes by AC (rf oscillating, non-static) and DC (non oscillating, static) electric fields. A power source electrically connected between the two cap-shaped metal electrodes 2 and the ring-shaped electrode 1 provides the necessary voltage bias between the electrodes, as shown in FIG. 1.

A charged particle located between the electrodes will experience a force due to the quadrupole electric potential. This force will cause the charged particle to become confined to a volume in the center of the trap significantly smaller than the dimensions of the trap itself In the context of this invention, the term "trapping volume" and its variations refers to the volume to which a charged particle is localized after a short time.

Such devices in a macroscopic scale have been widely fabricated and have proven to be a powerful tool in storage and detection of a single ion. Their typical dimensions are 100 μm to 1 cm, with voltages $V_{ac}$ in the range of 100-300 V, $V_{dc}$ in the range of 0-50 V and the AC frequencies $f = \Omega/2\pi$ in the range of 100 kHz-100 MHz.

If an electric bias of $\Phi_0 = V_{dc} - V_{ac} \cos(\Omega t)$ is applied to the system in FIG. 1, the resulting azimuthally symmetric electric field is given by its components.

$$E_z = \frac{V_{dc} - V_{ac}\cos(\Omega t)}{z_0^2}z, \quad E_r = \frac{V_{dc} - V_{ac}\cos(\Omega t)}{2z_0^2}r$$

Due to a periodic change in the sign of the electric force, one gets focusing and defocusing in both the r and z directions alternating in time. The equations of motion of a particle with mass M and charge Q in this field are given by Mathieu differential equations of motion, even in the presence of a damping force. This damping force, for example, can arise from collisional cooling in a gaseous environment or viscous forces in a liquid environment. If such a viscosity force is modeled by F=−Dv, where v is the instantaneous velocity of the particle in the trap, and D is a constant proportional to the viscosity constant and geometrical features of the particle, the Mathieu equations of the damped motion of the particle, $u=w\exp(-k\tau)$, are $$\frac{d^2w}{d\tau^2} + (a - k^2 - 2q\cos(2\tau))w = 0$$

Where u stands for either the r or z coordinate, $k=D/M\Omega$, $\tau=\Omega t/2$, and $$a = 4\frac{Q}{M}\frac{V_{dc}}{z_0^2}\frac{1}{\Omega^2}, \quad q = 2\frac{Q}{M}\frac{V_{ac}}{z_0^2}\frac{1}{\Omega^2}$$

Here $a_z=-2a_r$, $q_z=-2q_r$. The stability of the solutions to the equations, which defines the confining functions of the trap, is dependent on the values of parameters a, q, and k i.e. the stability depends on the magnitudes of both AC and DC components of the applied bias, on the angular frequency $\Omega$, on the trap dimensions, on the particle charge Q and its mass M, as well as of the viscosity of the liquid, defined here by D.

As a direct result of these stability parameters, it is possible to use a Paul trap to selectively trap particles. This is possible because different types of charged particles will vary in their charge to mass ratio Q/M. Because this characteristic influences stability, appropriately tuning parameters such as the $\Omega$, $V_{dC}$, or $V_{ac}$ will create a trap that attracts one type of particle while repelling another type of particle. This property has is very desirable for sorting applications, including, for example, separating biomolecules in aqueous solutions.

In the presence of a damping force, the regions in a-q-plane of the stable confinement are both enlarged and shifted in comparison to those with no damping. The solutions u may be bounded (stable) even if w is unbounded (unstable), due to the damping factor $\exp(-k\tau)$. The effect of the collisions between the trapped particle and background particles will change the stable orbit of the particle, statistically increasing or decreasing its energy, which depends on the relative mass of the particles. For target particles larger than the background particles, such as biomolecules in water, this results in a damping force. The solution generally oscillates with a system "secular" frequency $$\omega = \beta\frac{\Omega}{2}, \quad \text{where}$$

$$\beta \approx \left[\frac{a - k^2 + \frac{q^2}{2}}{1 - \frac{3q^2}{8}}\right]^{1/2}$$

on which there is superimposed micromotion (of much higher frequencies $\Omega$ and $2\Omega$).

Figure 9A:
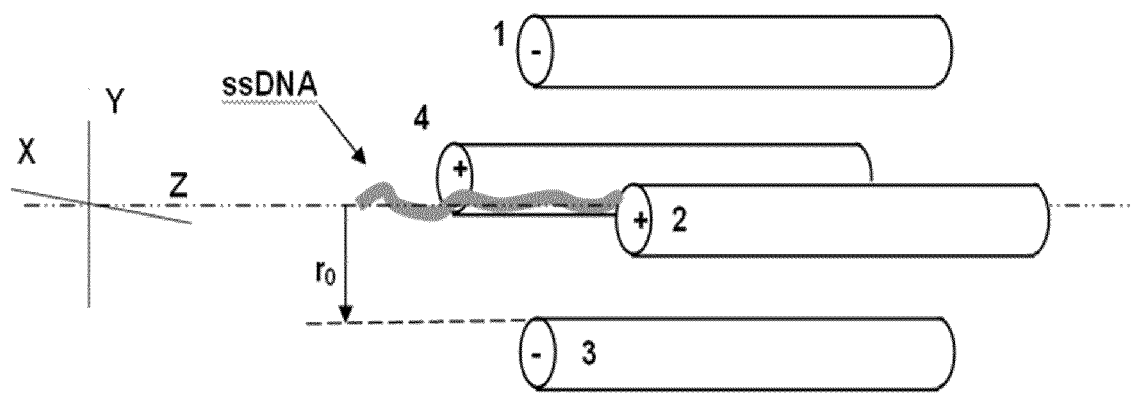
FIG. 9A illustrates a 2D Paul trap trapping a Single-Stranded DNA.

Variations of the Paul trap involving more electrodes are possible. One common variation is the 2D Paul trap, which is also quadrupolar but with the parameters $\alpha=1=-\beta$, $\gamma=0$. In this geometry, four confining electrodes are positioned around the trapping volume so that the quadrupole electric potential formed between them is orthogonal to the longitudinal axis of the trapping volume. One version of the 2D Paul trap, shown in FIG. 9A, is composed of cylindrically shaped electrodes extended in the z direction. This configuration provides trapping in the x and y directions without exerting a force in the z direction. Stable trapping in the x and y direction is determined by the values of a and q as determined above.

Figure 9B:
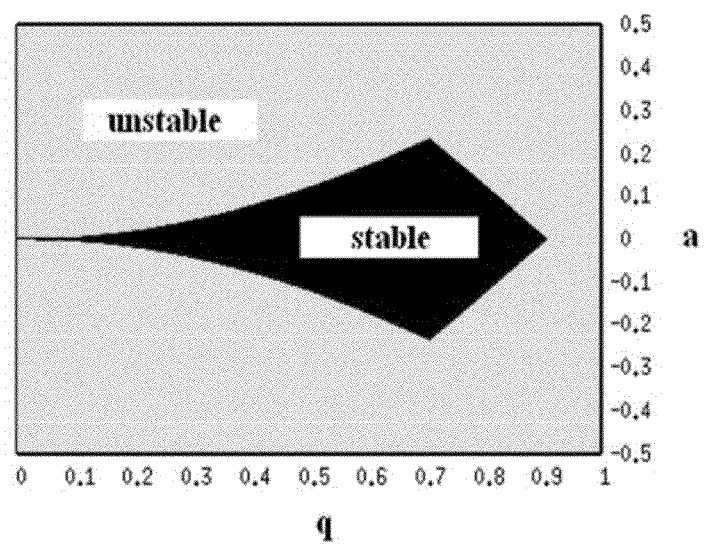
FIG. 9B illustrates the stability diagram for a 2D Paul trap.

FIG. 9B shows the regions in a-q-plane exhibiting stable and unstable confinement for such a 2D Paul trap in vacuum. In presence of liquid with various viscosity factors, the region of stability significantly changes and extends, as shown in FIGS. 9C and 9D.

Figures 15A, 15B, 15C:
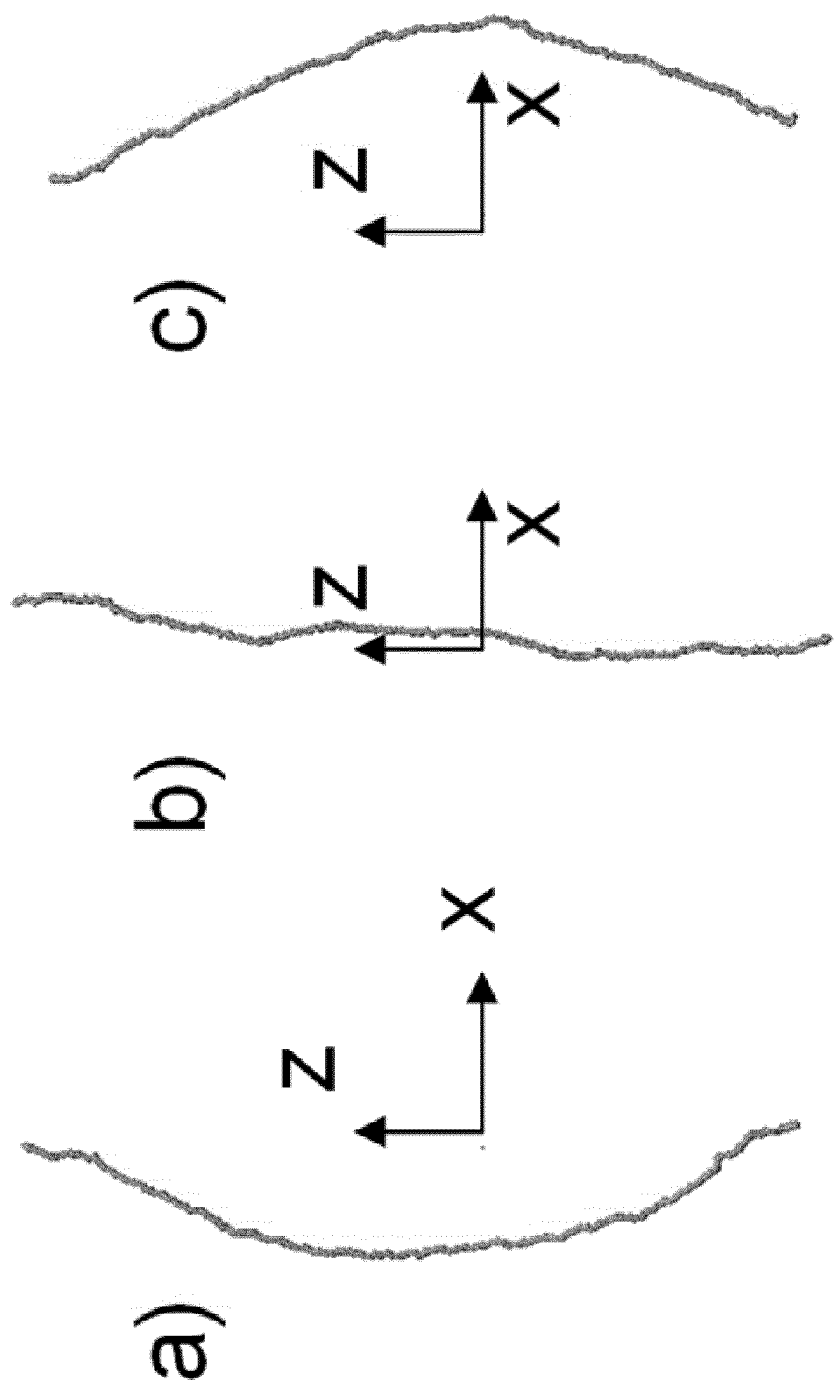
FIGS. 15A-15C illustrate the oscillations of a Single-Stranded DNA inside a 2D Paul trap.

Trapping only in two dimensions can be beneficial because in some cases, such as trapping DNA, a trapping force exerted along the z axis may cause deleterious folding or rotation. Simulations of long DNA segments trapped in a 2D Paul trap have been performed in vacuum, the details of which can be found in sections three and four of Sony Joseph et at 2010 *Nanotechnology* 21 015103, incorporated herein by reference for all purposes. A polymer such as DNA behaves like a line charge within the trap, shown in FIG. 9A, and can be effectively trapped under conditions similar to a single charged particle of the same Q/M ratio. The DNA undergoes both oscillations and rotations in the trap depending on its initial angle, position and velocity, as well as of the angular bonding force of the adjacent atoms. These oscillations can be seen in FIGS. 15A-C.

Free motion in the z direction in a 2D trap can be advantageously used for movement of the molecule into and out of the trap while maintaining a lateral confinement sufficient for measurement of particle properties. Motion of the charged particle in the z direction may be controlled by an appropriate DC field applied in the z direction. Alternating this DC field can allow the charged particle to be moved back and forth along the z axis. If a sensor is placed so that the charged particle passes by the sensor, such repeated trips past the sensor allow for multiple measurements and improvements in accuracy.

Still further variations of the Paul trap include configurations which generate multipole potentials of a higher order than a quadrupole potential in the trapping volume. Multipoles of different orders include, for example, quadrupoles and octopoles. These potentials can be created by positioning more electrodes around the trapping volume. While the equations of motion are no longer given by Mathieu differential equations, the resulting alternating potential exhibits similar trapping capabilities. These multipole Paul traps can be thought of as a generalization of the basic Paul trap quadrupole configuration. In order to trap a charged particle, the trap must be at least a quadrupole.

In some embodiments of the present invention the Paul trap is microscopic or nanoscopic. Reduced dimensions of the Paul trap allow for integration of the trap with other system components and provide trapping of charged particles in trapping volumes sufficiently small for detection or measurement of the charged particles. The trapping volume is a fraction of the size of the trap dimensions, typically a few percent of the size. This means that fabrication requirements are relaxed significantly compared to other trapping schemes in which the trapping volume is roughly the same size as the trap dimensions.

The Paul trap can operate in liquid environments. In some embodiments, the liquid is a solvent containing an electrolyte. In a preferred embodiment, the liquid is an aqueous solution. This environment is particularly useful for trapping biomolecules, as many of these biomolecules become charged in such an aqueous solution. In other embodiments, the liquid may be glycerin or another viscous liquid. In the case of a Paul trap operating in a liquid environment, the space between the electrodes contains a liquid which carries the charged particle being trapped. In the context of this invention, the term "liquid container" and its variations refer this central portion of the trap when the Paul trap is adapted to operate in a liquid environment. The liquid container supports the liquid in the center of the trap so that the charged particle in the liquid can be trapped. The liquid container may comprise structures of the Paul trap such as the confining electrodes themselves or oxide layers which isolate the electrodes. The trapping volume is inside of the liquid container, so that a charged particle present in the liquid container can be pulled into and confined within the trapping volume. The liquid container may be fluidly connected to a microfluidic channel or other means for providing a liquid into the liquid container.

During operation, the liquid is provided to the Paul trap. If the liquid container of the Paul trap is connected to a microfluidic channel, the liquid containing the charged particle to be trapped is provided through the microfluidic channel. Once the periodic bias is applied to the electrodes of the Paul trap, an electric potential is generated between the electrodes. Eventually, the charged particle will be enter the space between the electrodes and experience the electric potential. Due to the multipole form of this potential, the charged particle will move into the trapping volume and be trapped.

Molecular Dynamics simulations of two nanoscale 3D Paul traps are shown in FIGS. 2-8 and illustrate the trapping function of the Paul trap on a Chlorine ion in vacuum and in an aqueous environment. These traps were of the 3D Paul trap configuration and constructed from gold atoms, with 2 nm diameter holes in the centers of each cap-shaped electrode to approximate an entrance and exit for the trapped ion. The two traps had dimensions, $2r_0=5$ nm, $2z_0=5/\sqrt{2}$ nm (nanotrap A), and $2r_0=50$ nm $2z_0=50/\sqrt{2}$ nm (nanotrap B). The parameters a and q were chosen in the middle of the stable region as defined for a conventional Paul trap, i.e. a=0.25 and q=0.4. Further details on the simulations can be found in sections two and three of Xiongce Zhao and Predrag S Krstic 2008 *Nanotechnology* 19 195702, incorporated herein by reference for all purposes.

Figure 2:
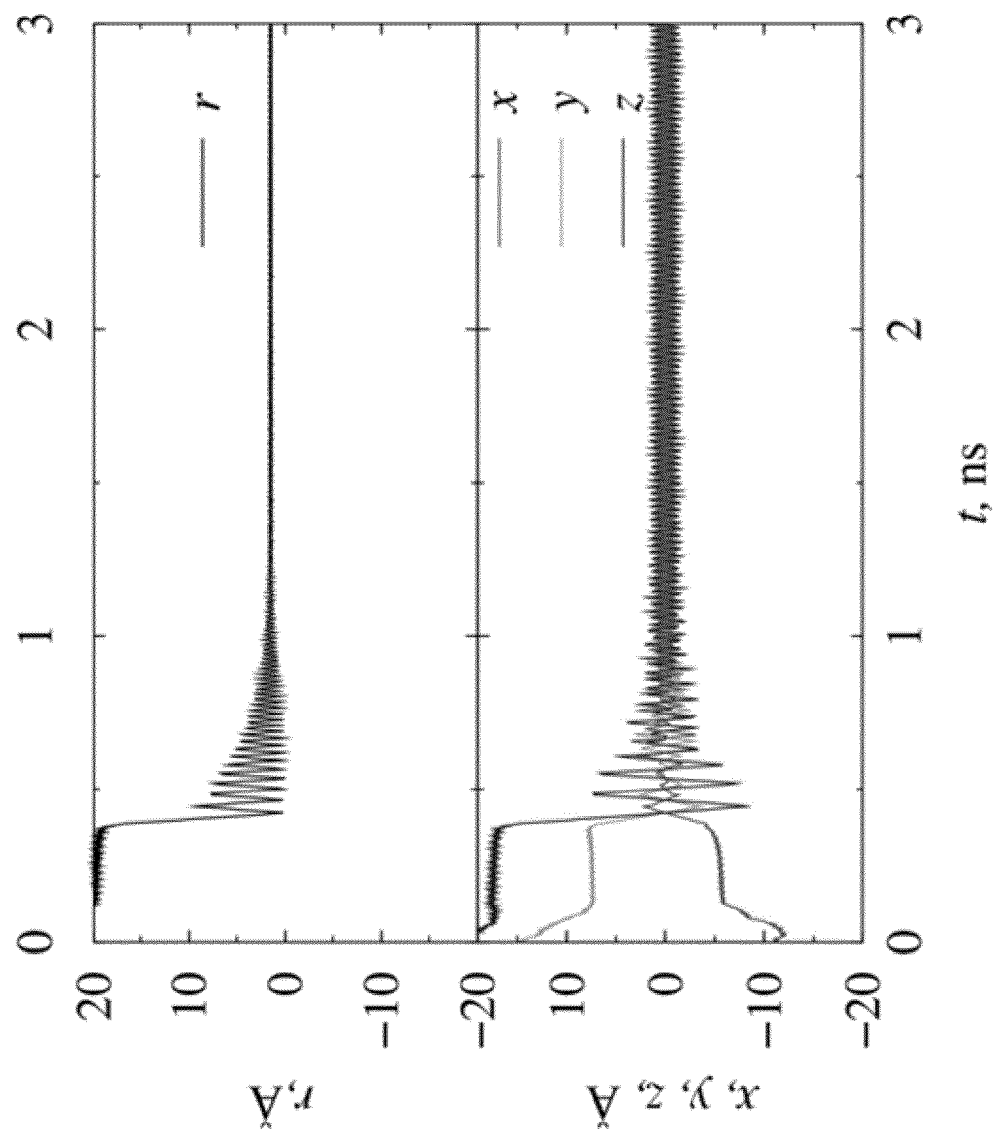
FIG. 2 illustrates the position of a Chlorine ion in a nanoscopic Paul trap over time.

FIG. 2 shows coordinates of the ion as function of time in trap A at temperature of 3 K (corresponding to the ion energy of $2.5 \times 10^{-4}$ eV). The initial coordinates shown have values (−12, 15, 24) Å relative to the geometric center of the trap, which were randomly set at the beginning of the simulation. The initial momentum of the ion was randomized following a Gaussian distribution but conformed to the system temperature. The needed trapping field is approximately $V_{dc}=200$ mV and $V_{ac}=600$ mV, with the chosen frequency of AC voltage being 318 GHz. The trajectory of the ion was monitored for up to 3 ns of simulation. As can be seen in FIG. 2, the chlorine ion is driven to the center of the trap and rotated in a circular motion with its stabilized distance to the trap center being about 1.5 Å. The time of 1.2 ns is elapsed before the stabilization is reached. The oscillation frequency of the trajectory is about 50 GHz, which is quantitatively consistent with the estimated "secular" frequency ω, for the given values of (a,q, k=0,Ω). Repeated runs lead to the same quantitative conclusions as the one shown, contributing to a statistical weight of the results.

Figure 3:
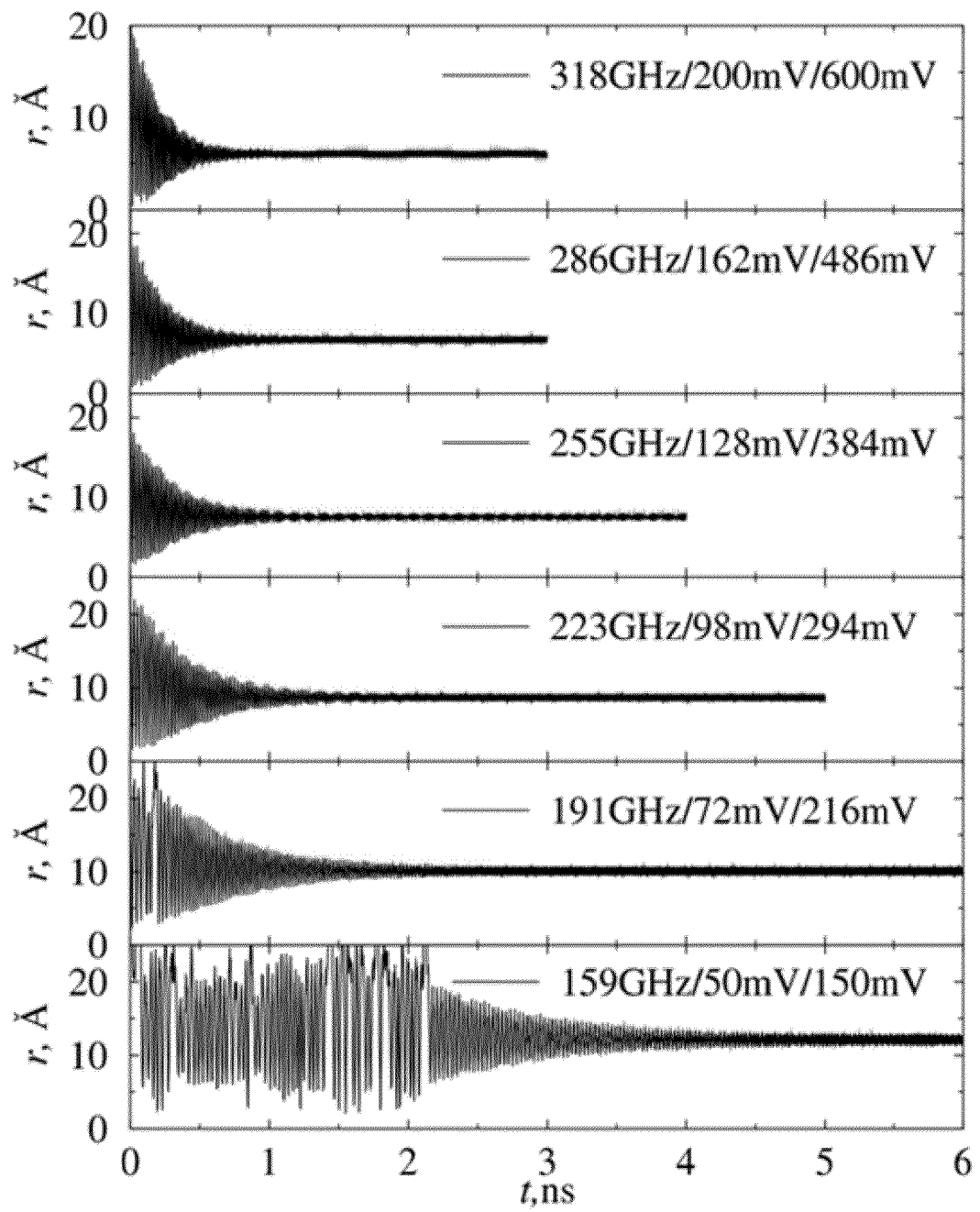
FIG. 3 illustrates the effects of different trap parameters on the position of a Chlorine ion in a Paul trap over time at 50 K.

A series of simulations was performed by varying the driving fields from ($V_{dc}=0.5$ mV, $V_{ac}=1.5$ mV) to ($V_{dc}=200$ mV, $V_{ac}=600$ mV), and with frequencies ranging from 16-318 GHz. The AC voltage with a frequency in tens to hundreds of GHz is required in order to trap the charged ions within a timescale of nanoseconds. An increase in frequency, which also implies an increase in the magnitude of the voltage for given a and q, results in a faster establishment of stabilization. FIG. 3 shows simulations with AC voltage frequencies in the range of 159-318 GHz, which require voltages of $V_{dc}=50$ mV, $V_{ac}=150$ mV to $V_{dc}=200$ mV, $V_{ac}=600$ mV, at a constant temperature of 50 K (i.e. equivalent ion energy of $4.3 \times 10^{-3}$ eV). The stabilization time for these systems ranges from 4.5 ns to 1 ns. However, the amplitude of the stabilized ion "secular" oscillations ranges from 12 Å to 6 Å, well below the dimensions of the trap.

Figure 4:
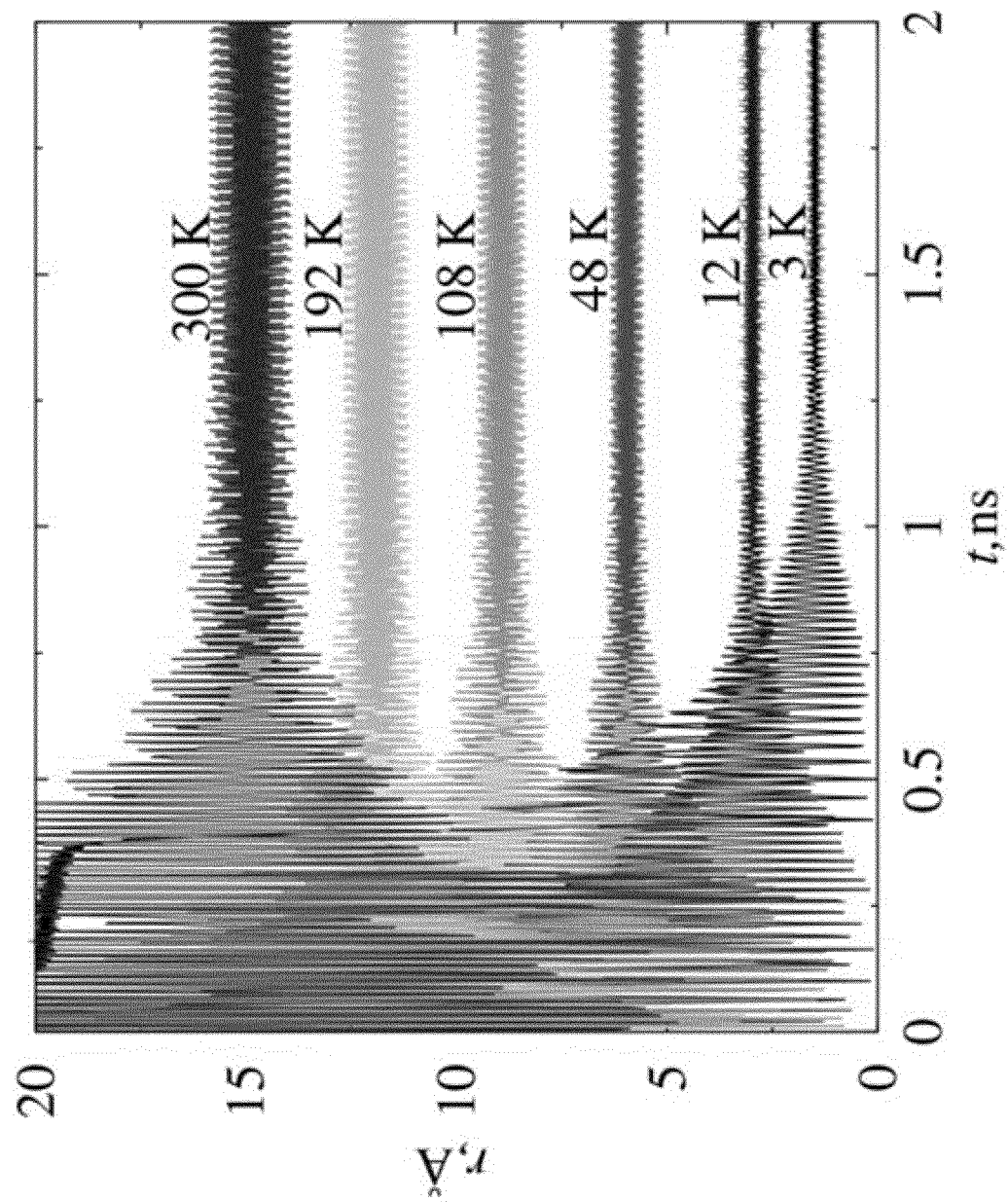
FIG. 4 illustrates the effect of temperature on stabilization time in a Paul trap.
Figure 5:
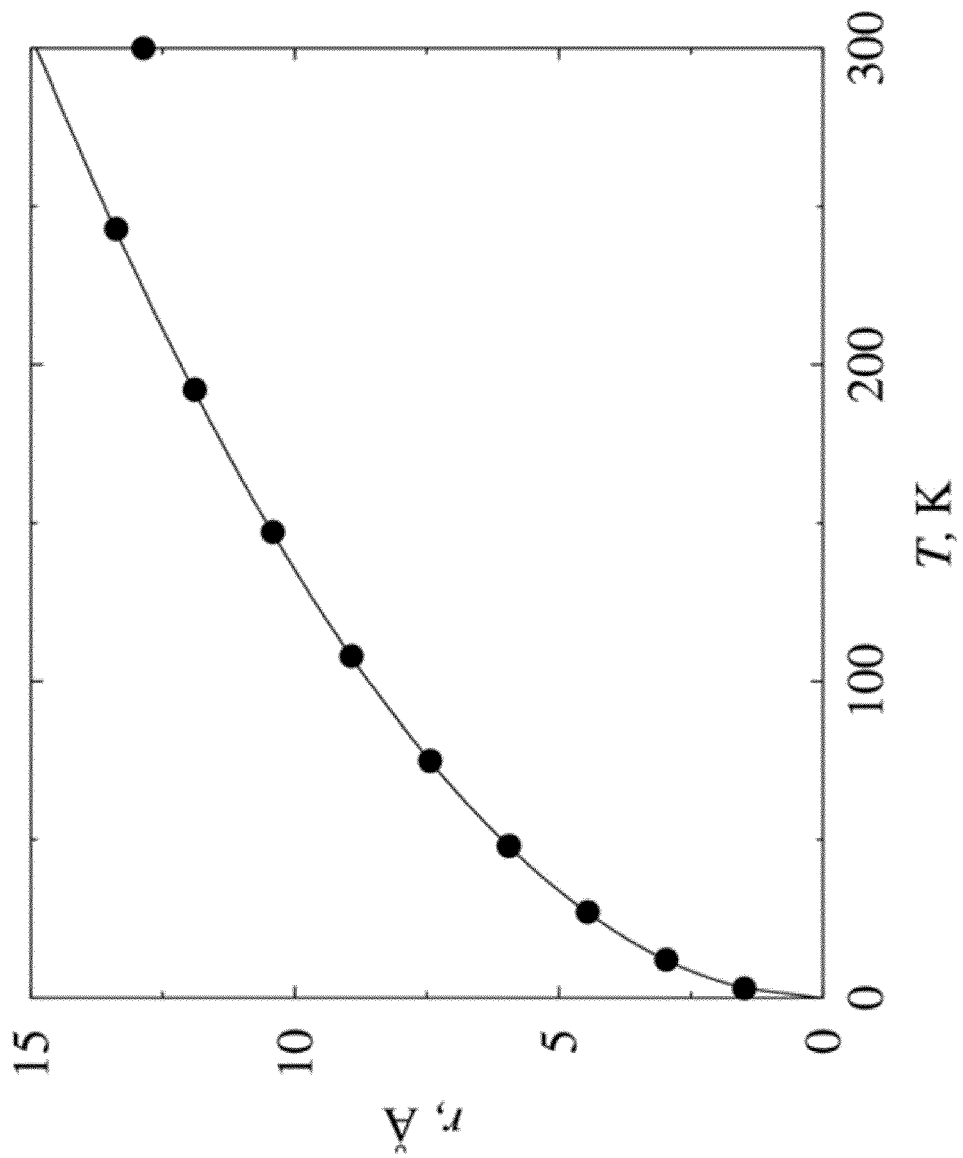
FIG. 5 illustrates the oscillation amplitude for various temperatures.

The stabilization time is dependent on the temperature, i.e. on the initial ion kinetic energy. FIG. 4 shows such variation of the initial ion energy in the range of 3-300K in trap A for $V_{dc}=200$ mV, $V_{ac}=600$ mV, and f=318 GHz. There is an optimal temperature which yields the shortest stabilization time. For a chlorine ion under the above conditions the shortest stabilizing time occurs at 50 K, differing by almost a factor of 2 to the values at 3 K and 300 K.

The oscillation amplitude of the ion inside the trap is also strongly dependent on the temperature. For example, at 300 K the ion is orbiting with a radius of 15 Å, whereas at 3 K the orbiting radius is only about 1.5 Å. The dependence of the orbiting radius is related to the temperature by the equation $r^2 \propto T$. The results are plotted in FIG. 5. The simulated data point at 300 K does not overlap with the curve, simply because of the confinement effect of trap A. That is, the ion was not able to move beyond the trap cap along the z axis. Therefore, the effective circulating orbit of the ion at 300 K is depressed. In the 300 K case the orbiting trajectory of the trapped ion is changed slightly to adapt to the inner shape of the trap, although the circular nature of the orbit is not changed. In other words, the motion of the ion depends on the trap size. This phenomena will not be present for a macroscopic Paul trap but becomes significant when the trap is nanoscopic. This effect implies that a larger trap will tolerate an input ion with a higher energy, therefore higher temperature, without disturbing its orbiting motion in the z direction.

Figure 6:
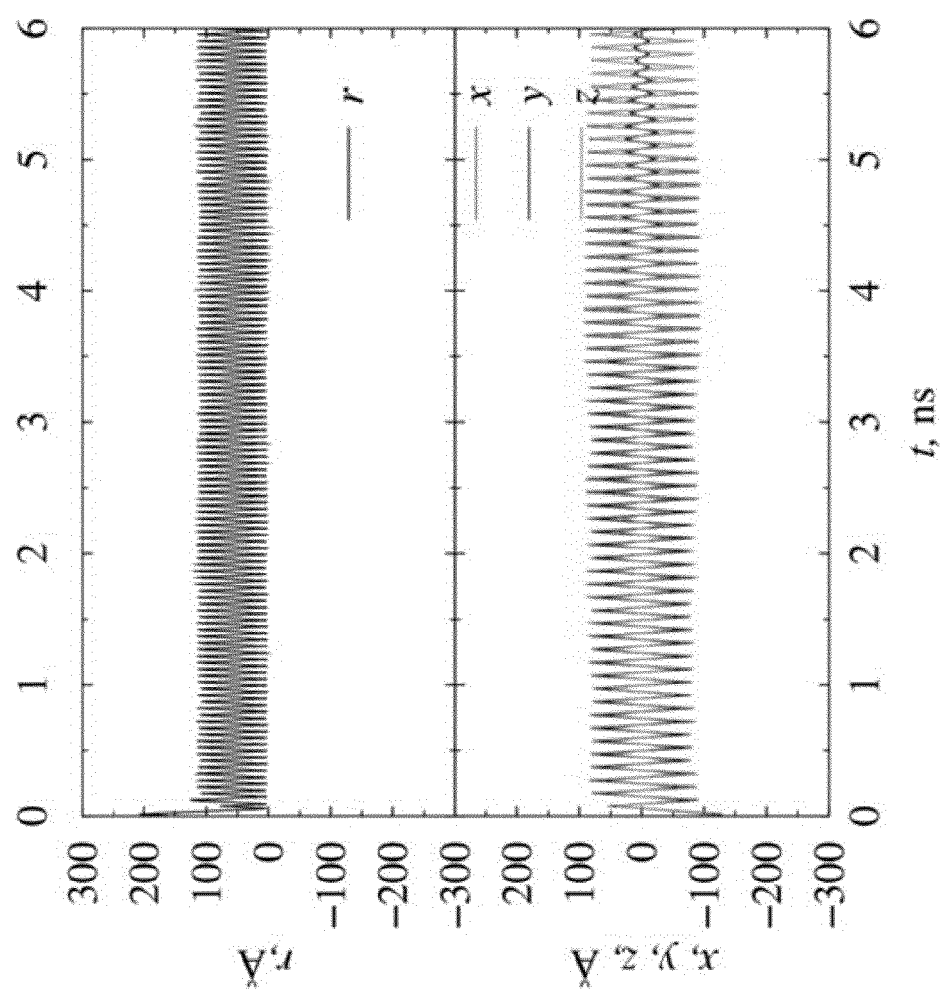
FIG. 6 illustrates the position of a Chlorine ion in a Paul trap over time.

FIG. 6 shows the trapping of a chlorine in trap B in vacuum. The increased dimensions of the trap allowed for lower trapping field frequencies, here chosen to be 20 GHz, and larger electric biases before a possible breakdown occurs. The ion was initially positioned at (−110, −100, 88) Å and the initial kinetic energy of the ion conforms to a system temperature of 300 K. The trapping fields were $V_{dc}=80$ mV, $V_{ac}=240$ mV, which were turned on at t=0. As shown in FIG. 6, the ion was trapped in the center of the trap after a short time, with the orbital radius of about 6.5 nm. The overall behavior of the ion motion is similar to that observed in trap A, only with much bigger orbiting amplitudes.

Figure 7:
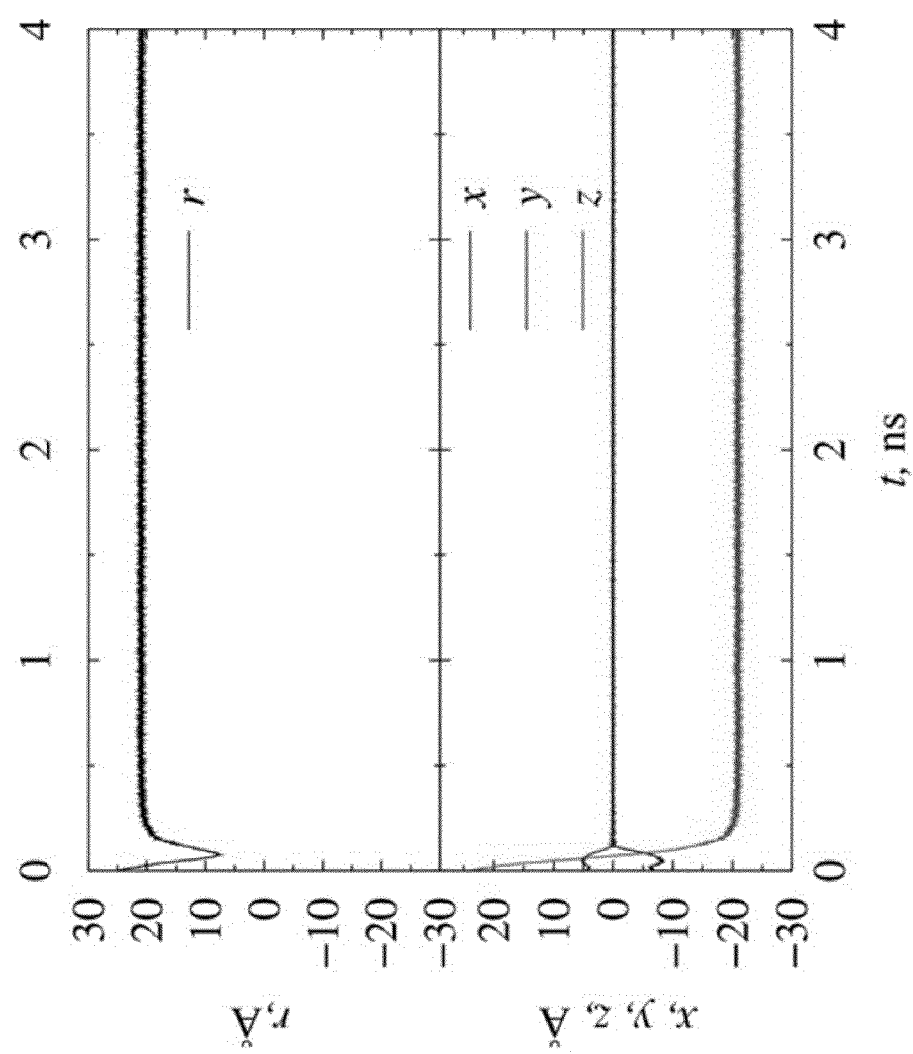
FIG. 7 illustrates trapping in a Paul trap in the presence of a longitudinally driving DC field.

FIG. 7 shows a the trapping of a chlorine ion in trap A with an additional driving DC field along the z-axis (see FIG. 1) ranging from 10-150 mV/nm, which illustrates the impact of this additional field on the trapping process. Initially the ion was placed at the entrance of one of the cap holes with its coordinate as (5, −7, 22) Å relative to the trap center, with initial momentum of the ion set to conform to the system temperature as before. The z-direction driving field and the trapping fields were turned on simultaneously when the simulation started, and the trajectory of the ion was monitored for 3-12 ns. The near zero temperature of 3 K gives a clear picture of how the ion moves along each direction under the influence of the additional z-direction field. As seen in FIG. 7, the ion migrates through the central region from one entrance, while orbiting around the trap center in the x-y plane. The ion was finally stabilized at a position of about (0, 0, −21) Å, with the orbiting radius of about 2.1 nm. The ion is trapped similarly to a trap without the additional z-direction DC field although its position is now significantly shifted along the z-axis. The shift of the ion orbit along the z-axis varies with the strength of the field.

Additional simulations indicate that the ion is stably trapped when the z field is below 110 mV/nm, while a field of 125 mV/nm would drive the ion all the way through the trap within 1 ns, without reaching stabilization. This suggests that for trap A the threshold driving DC field for moving the ion through the whole trap along z-direction lies between 110 to 125 mV/nm. By changing the polarity of the driving DC field it is possible to drive the ion back and forth along the z-axis through the trap. This back and forth movement provides an opportunity to increase the certainty of a measurement taken of the trapped ion inside the trap.

Figure 8:
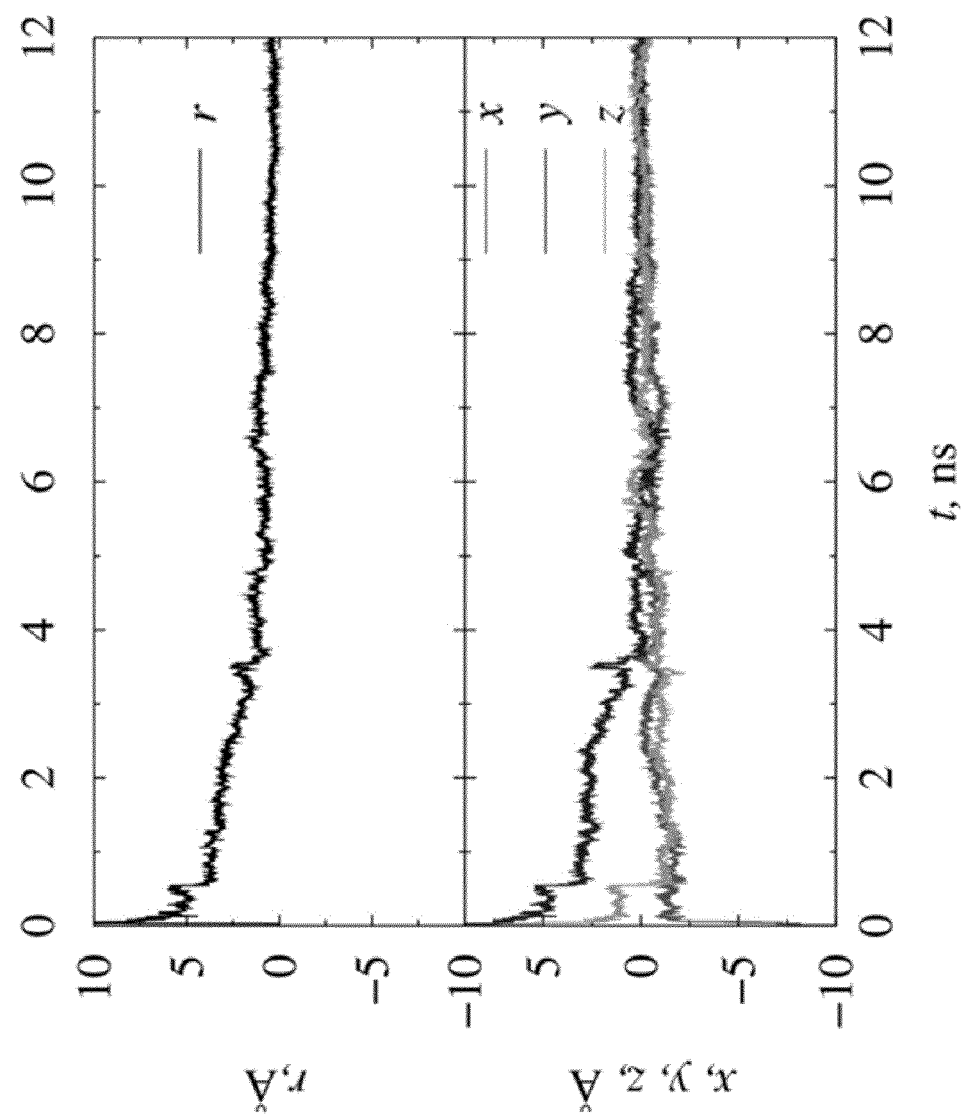
FIG. 8 illustrates the trapping of a Chlorine ion in a Paul trap containing water.

FIG. 8 shows the trapping of a chlorine ion inside trap A filled with water, at 300 K with $V_{dc}$=4V, $V_{ac}$=12V, f=80 GHz. Solvent polarization effects as well as impact from the collisions and thermal fluctuations of water molecules were treated through explicit atomistic MD simulations, using 5108 water molecules filling the volume of the trap. The trajectory of the ion shows that the stabilization process takes a much longer time than in vacuum even with stronger trapping electric fields. It takes about 12 ns for the ion to be trapped stably in the center of trap A. On the other hand, the ion experiences less fluctuations in movement during the stabilizing process along any of the directions, with a much smaller final oscillation amplitude of the ion in comparison to the same ion trapped in vacuum at the same temperature. One possible reason for such an effect is that the motion of the ion was effectively thermalized by water molecules around it due to the strong collision force from the electrostatic interactions. This shows the effects of background damping on the ion motion in the trap, suggesting that the addition of the solvent to the trap helps to stabilize the ion motion.

Figure 10A:
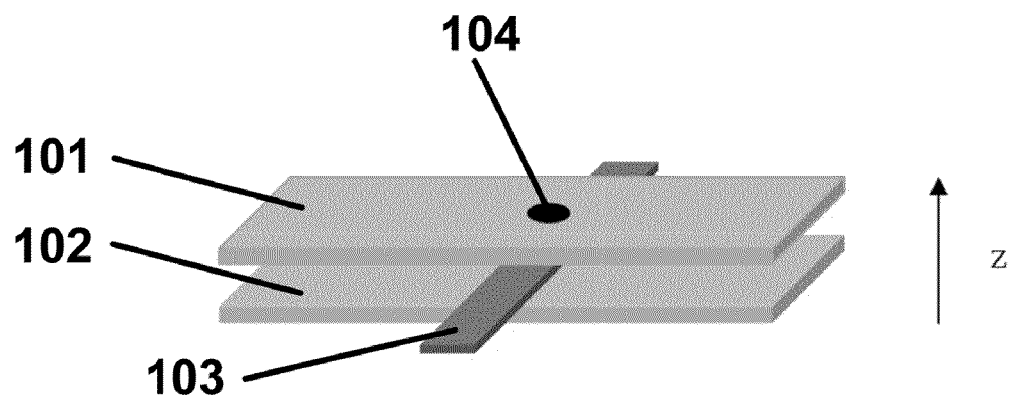
FIG. 10A-10B illustrate various views of a 3D nanopore Paul trap.
Figure 10B:
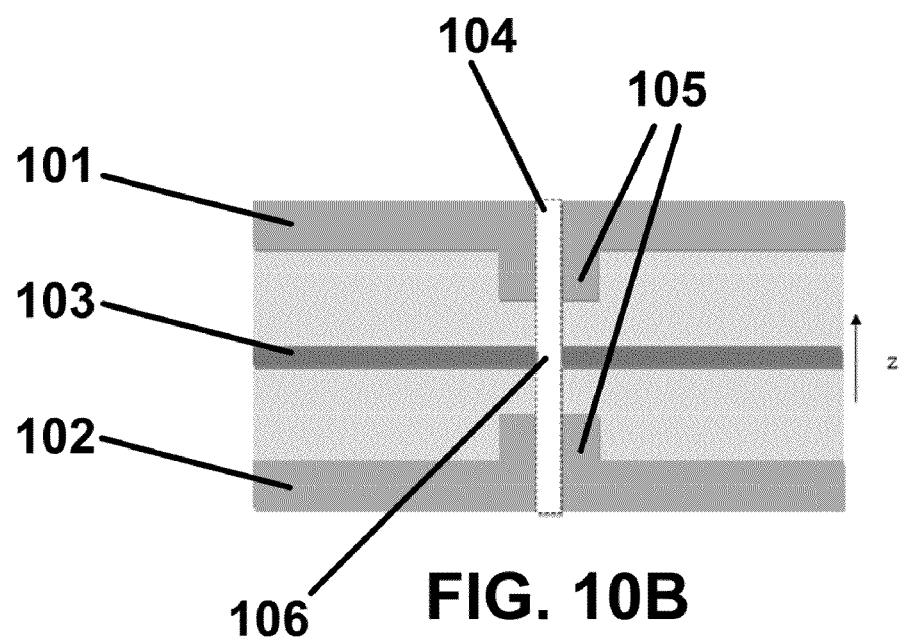

FIG. 10A-B show a 3D Paul trap implemented using conventional metal/insulator microfabrication approaches. This tri-layer crossing metal/insulator structure is used to form the Paul trap structure by etching nanopore 104 at the crossing of three metal electrodes. Nanopore has a diameter of approximately 20-50 nm, which is smaller than the widths of the three metal electrodes. Top electrode 101 and bottom electrode 102 act as the laterally confining electrodes. Middle electrode 103 forms the transversely confining ring electrode. A power source is electrically connected to the electrodes such that an AC and DC bias is applied between the top electrode and the middle electrode, and between the bottom electrode and the middle electrode. This AC and DC bias creates the time-varying periodic quadrupole electric potential necessary for trapping a charged particle. The walls of nanopore 104, including the electrodes and oxide insulator, form the liquid container. Trapping volume 106 is within the liquid container.

The structure can be realized by a number of microfabrication approaches known in the art. The circular geometry necessary for a ring electrode necessary for the 3D Paul trap is achieved by a self-aligned etch through middle electrode 103. The top and bottom electrodes are realized by first creating the initial dielectric stack with the buried middle electrode, recessing from both sides a cylindrical etch pit (in which nanopore 104 will be centered), and backfilling with metal to make a pronounced quadrupole geometry. Middle electrode 103 is defined by a final etch through the structure creating the self-aligned translocation hole (nanopore 104) in the z-direction.

Preferably, top electrode 101 and bottom electrode 102 have linewidths between 1-2 μm, with recesses 105 that are 100 nm deep. Middle electrode 103 is preferably 25-35 nm thick. Reactive Ion Etching techniques, known in the art, can be used to etch the nanopore through the stack. These preferred ranges demonstrate one of the key benefits of a Paul trap, which is that the trapping volume is much smaller than the device itself. This allows for nanoscale control using much larger device structures.

Figure 11A:
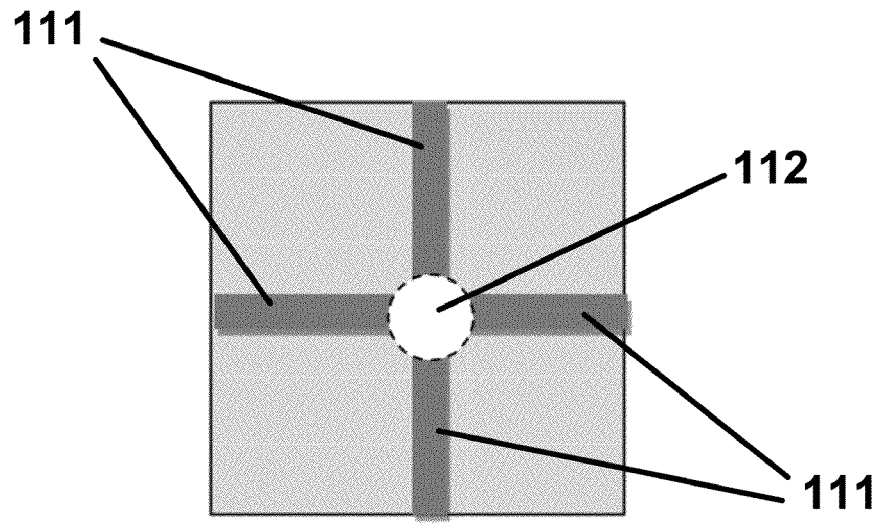
FIG. 11A-11B illustrate various views of a 2D nanopore Paul trap.
Figure 11B:
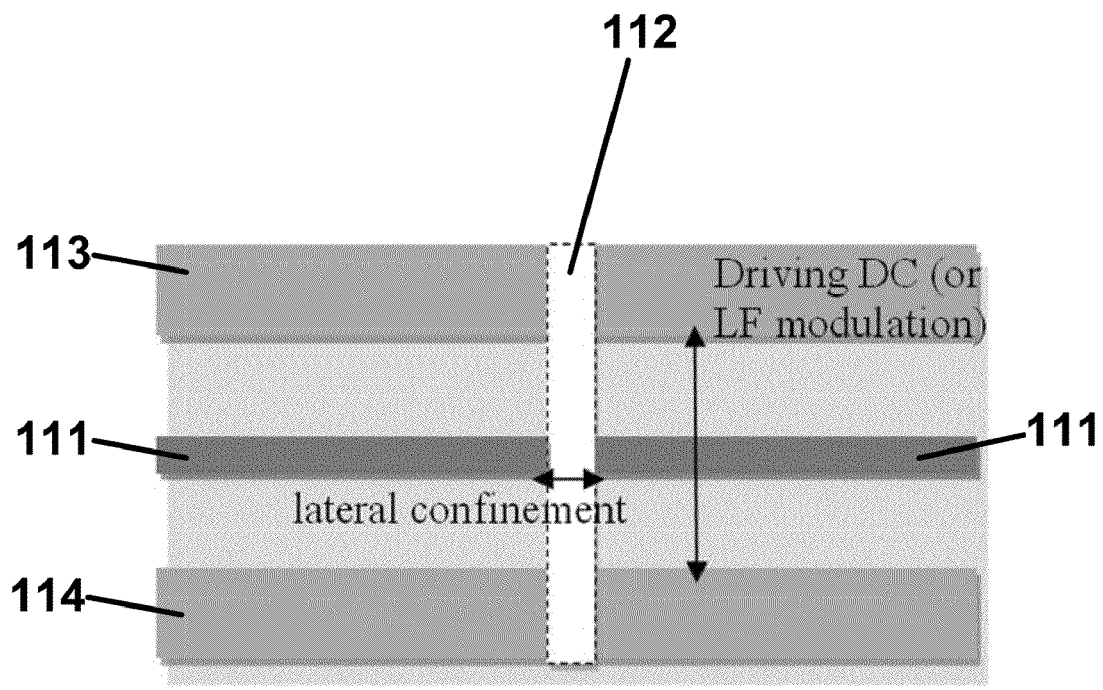

In another embodiment implemented with microfabrication techniques, a 2D Paul trap is generated at the intersection of metal electrodes. As shown in FIG. 11A, a nanopore is etched at the intersection to form four coplanar electrodes 111. A power source electrically connected to the four coplanar electrodes 111 applies a voltage bias between adjacent electrodes. This voltage bias creates a quadrupole electric potential inside nanopore 112, providing confinement. With reference to FIG. 11B, the 2D configuration does not provide confinement along the axis of nanopore 112, which is orthogonal to the plane of the electrodes. Top electrode 113 and bottom electrode 114 provide control of the charged particle in this dimension. These electrodes may be initially pre-etched, added later, or electroplated to allow good definition of coplanar electrodes 111. A number of process variants can be used for coplanar electrodes 111, including straightforward nitride/metal definition/cap dielectric, followed by reactive ion etching of the through hole and metallization for top/bottom; or a Si process using SOI (Silicon-On-Insulator) and potentially implanted lateral electrodes.

Figure 12A:
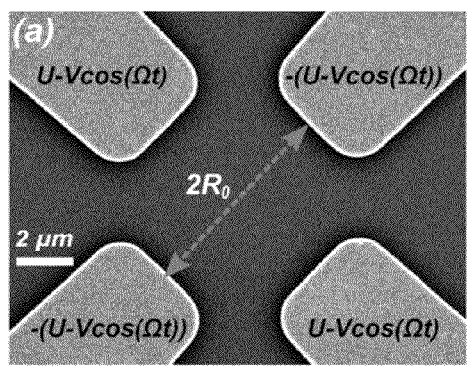
FIG. 12A-12B illustrate various views of a 2D planar Paul trap.
Figure 12B:
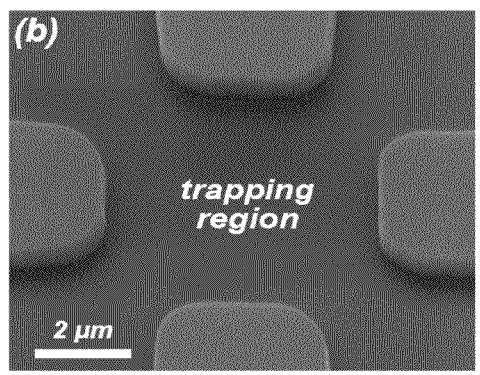
Figure 12C:
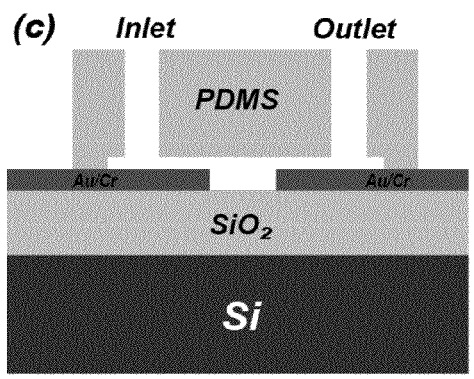
FIG. 12C illustrates a 2D planar Paul trap fluidly connected to a microfluidic channel.

In a preferred embodiment, shown in FIG. 12A-B, a 2D Paul trap is constructed by patterning electrodes on a $SiO_2$/Si wafer. Preferably, four Au/Cr (350/30 nm) electrodes are formed on top of this insulating substrate by UV-lithography and a double layer liftoff process. The tip to tip distance ($2r_0$) for each pair of opposite electrodes ranges from 2-8 μm. Rather than making use of a nanopore, the liquid container in this preferred embodiment is simply the electrodes themselves and the substrate. An aqueous solution flows through a microfluidic channel. FIG. 12C shows the integration of the 2D Paul trap with the microfluidic channel.

The microfluidic channel is formed by poly(dimethylsiloxane) (PDMS) using SU-8 as a molding master. Oxygen plasma treatment permanently bonds the PDMS onto the device surface and forms an anti-evaporation microfluidic channel. An inlet and an outlet are punched through before assembling.

The device is wire-bonded and mounted onto a printed circuit board (PCB). Voltage in the form of U−V cos(Ωt), produced by a function generator (Tektronix AFG3252) together with a voltage amplifier (Tabor Electronics, Model 9250), is delivered to the device through 50Ω BNC cable and monitored by an oscilloscope (Tektronix DPO 4104). Since only the voltage difference between electrode pairs is of importance, for simplicity, only one phase AC potential is applied to one pair of electrodes while the other pair is referenced to zero and set to ground. However, a two channel mode with two out-of-phase signal (U−V cos(Ωt) and −U+V cos(Ωt)) is also used in some cases (mainly to get higher voltage difference).

Particles in the microfluidic channel move freely in the x-y plane and into the liquid container within the trap, but are confined in the z direction by the channel height, which is controlled when fabricating the SU-8 master. The channel height is preferably less than 20 μm.

Figure 12D:
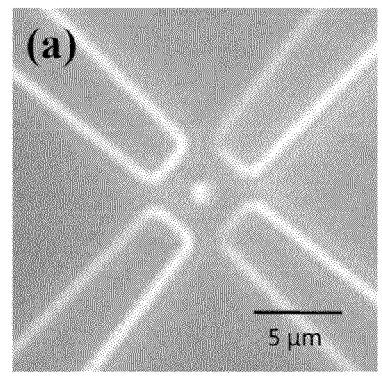
FIG. 12D illustrates a charged particle trapped in a 2D planar Paul trap.

FIG. 12D demonstrates the trapping functionality of the 2D Paul trap. The charged particle shown in FIG. 12D is a polystyrene bead in deionized water. The beads used had a mean radius of 490 nm and were functionalized with carboxylate groups (~COOH) which give rise to the charge of the particle. An individual bead can be held in the trap for periods up to several hours. While trapping mostly occurs for single beads due to inter-particle Coulomb repulsion, multiple beads can be simultaneously trapped.

In order to make use of this new technique for trapping charged particles in liquid environments, suitable methods for measuring properties of the trapped charges must be employed. In some embodiments, these measurements are optical measurements. In other embodiments, the measurements measure electronic properties of the charged particle.

It is possible to directly observe particles confined within the Paul traps using an optical microscope. Observation can be aided by using fluorescently-tagged molecules or colloidal quantum dots. For example, a fluorophore-tagged DNA strand can be observed as it passes through the Paul trap using a fluorescent microscope.

Figure 13:
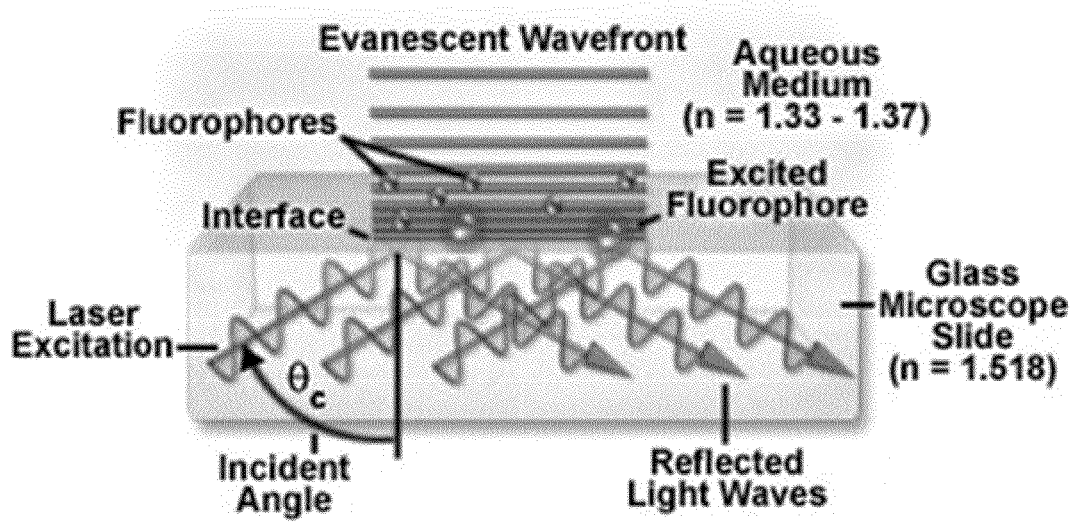
FIG. 13 illustrates the Total Internal Reflection Fluorescence technique.

Optical measurements with greater spatial detail can be obtained using total internal reflection fluorescence microscopy (TIRFM). This technique employs the unique properties of an induced evanescent wave to selectively illuminate and excite fluorophores in a restricted specimen region immediately adjacent to a glass-water (or glass-buffer) interface. TIRFM requires an excitation light beam traveling at a high incident angle through a solid glass coverslip. Refractive index differences between the glass and water phases regulate how light is refracted or reflected at the interface as a function of incident angle. At a specific critical angle, the beam of light is totally reflected from the glass/water interface, rather than passing through. The reflection generates a very thin electromagnetic field (usually less than 200 nanometers) in the (aqueous) medium, which has an identical frequency to that of the incident light. This field, called the evanescent wave or field, undergoes exponential intensity decay with increasing distance from the surface. A schematic of the TIRFM principles is shown in FIG. 13.

The characteristic distance for decay of the evanescent wave intensity is a function of the incident illumination angle, wavelength, and refractive index differences between media on each side of the interface. Fluorophores residing near the glass-liquid surface can be excited by the evanescent field, provided they have electronic transitions that occur in or very near the wavelength bandwidth. Fluorophores farther away from the surface avoid being excited, which leads to a dramatic reduction of unwanted secondary fluorescence emission from molecules that are not in the primary focal plane. The effect enables production of high-contrast images of surface events with a significant increase in signal-to-background ratio over classical widefield techniques.

The penetration depth d, which usually ranges between 30-300 nm, decreases as the reflection angle grows larger. This value is also dependent upon the refractive indices of the media present at the interface and the illumination wavelength. In general, the maximum value of d is on the order of the incident wavelength. This provides a wide range of possibilities to control the evanescent field and a field intensity dependent tag response for the z-localization of the tagged molecule.

Figure 14A:
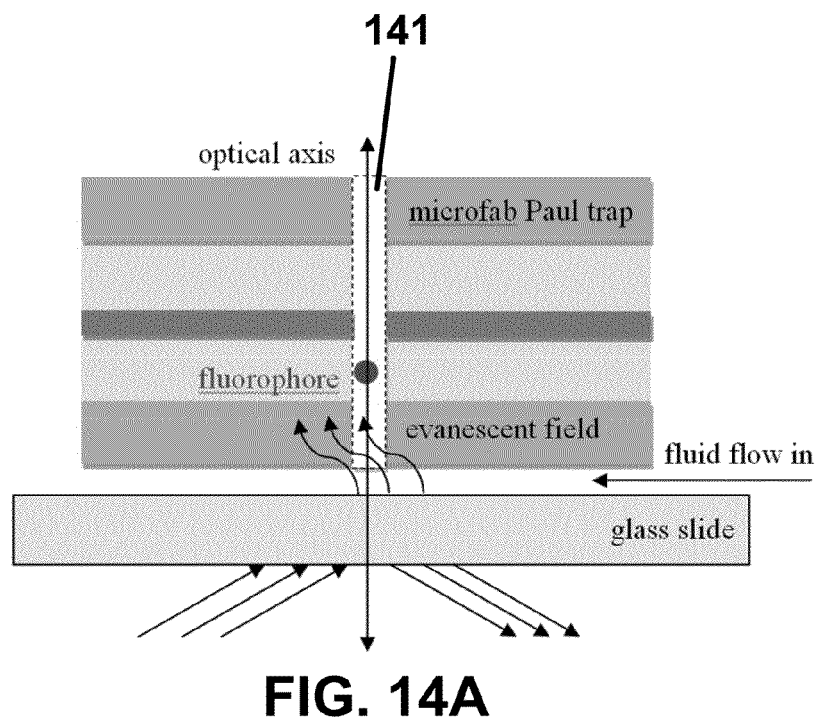
FIG. 14A-14B illustrate a system combining Paul trapping with Total Internal Reflection Fluorescence techniques.

In one embodiment, TIRFM is used in conjunction with a microfabricated Paul trap to observe fluorophore-tagged ssDNA. The microfabricated Paul trap is flip-chip mounted on a glass slide with surface-etched microfluidic channels for fluid flow, as shown in FIG. 14A. Fluid containing the fluorophore-tagged ssDNA flows into the liquid container 141 of the Paul trap. In this configuration the Paul trap is a 2D type where the liquid container is a nanopore. As the z-position of the tag is moved into and out of the evanescent field, the fluorescence is detected by a microscope on the optical axis. Because the excitation intensity is exponential with distance, the intensity versus the trap position setting can be measured. Nanoscale resolution is achieved, due to the lateral localization from the 2D Paul trap in conjunction with precise lateral position data from the exponential field intensity. Since evanescent fields propagate hundreds of nanometers in this system, it is possible to follow the ssDNA molecule all the way through the trap. An additional feature the trap system, not usual for TIRF microscopy, is that the longitudinal position of the particle can be independently tuned allowing for very high spatial resolution.

Figure 14B:
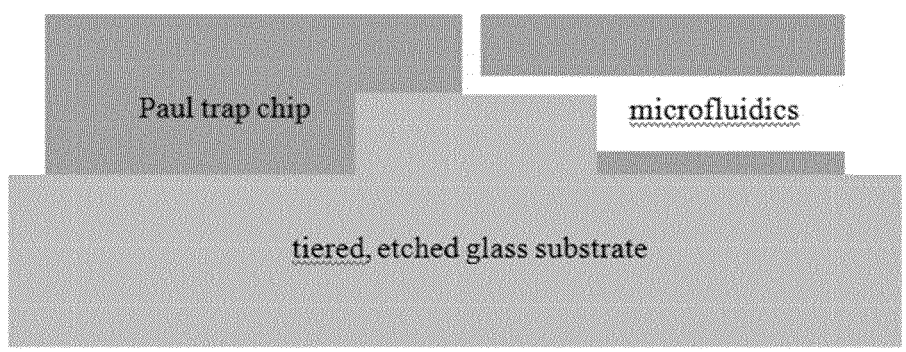

A viable system for conducting TIRF measurements on trapped particles requires the evanescent field extend into the center of the trap. Because the range of the evanescent field is only 30-300 nm away from the glass, this presents difficulties with regards to mechanical stability, fluid flow resistance, and electrode lead fanout. In a preferred embodiment, shown in FIG. 14B, a pre-fabricated tiered glass mounting substrate is used. This structure allows the central trap region to be within the TIRF evanescent field while also allowing many microns of thickness for stability, fluid channels, and electrodes.

Another class of measurements which can be done on trapped particles are electrical measurements. In nanoscale dimensions electronic properties such as capacitance and conductance are strongly influenced by the quantum mechanical structure of the molecules being measured. Because the atomic structures of molecules are different, under the right conditions they can be distinguished from one another.

REFERENCES CITED

All references cited herein are incorporated herein by reference in their entirety and for all purposes to the same extent as if each individual publication or patent or patent application was specifically and individually indicated to be incorporated by reference in its entirety for all purposes.

EQUIVALENTS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A system for trapping a charged particle in a trapping volume comprising:
   (a) at least three confining electrodes distributed around the trapping volume;
   (b) a liquid container adapted to hold a liquid carrying the charged particle between the at least three confining electrodes; and
   (c) a power source electrically connected to the at least three confining electrodes, wherein the power source is capable of applying a time-varying periodic voltage bias between the at least three confining electrodes for creation of a time-varying periodic multipole electric potential in the trapping volume, wherein the multipole electric potential is at least a quadrupole.

2. The system of claim 1, wherein the liquid container is fluidly connected to a microfluidic channel for supplying liquid to the liquid container.

3. The system of claim 1, wherein the trapping volume is microscopic.

4. The system of claim 1, wherein the trapping volume is nanoscopic.

5. The system of claim 1, wherein the liquid container is adapted to hold a liquid solution comprising an electrolyte.

6. The system of claim 1, wherein the at least three confining electrodes are N confining electrodes positioned around the trapping volume so that the multipole electric potential in the trapping volume is orthogonal to a longitudinal axis of the trapping volume, wherein N is an even whole number of four or greater.

7. The system of claim 6, wherein the N confining electrodes are coplanar in a plane orthogonal to the longitudinal axis of the trapping volume.

8. The system of claim 7, further comprising:
(d) two electrodes arranged along the longitudinal axis of the trapping volume so that the trapping volume is between them; and
(e) a power source electrically connected to the two electrodes arranged along the longitudinal axis of the trapping volume, wherein the power source is capable of applying a voltage bias for controlling the movement of the charged particle along the longitudinal axis of the trapping volume.

9. A system for trapping a charged particle comprising:
(a) two longitudinally confining electrodes arranged along a longitudinal axis;
(b) a transversely confining electrode encircling the region between the two longitudinally confining electrodes transversely to the longitudinal axis;
(c) a liquid container adapted to hold a liquid carrying the charged particle between the two longitudinally confining electrodes and the transversely confining electrode; and
(d) a power source electrically connected to the longitudinally confining electrodes and the transversely confining electrode, wherein the power source is capable of applying a time-varying periodic voltage bias to create a time-varying quadrupole electric potential in the trapping volume.

10. The system of claim 9, wherein the liquid container comprises a nanopore.

11. The system of claim 9, further comprising a sensor adjacent to the trapping volume for measuring a property of the charged particle.

12. The system of claim 11, wherein the property measured by the sensor adjacent to the trapping volume is the transverse conductivity.

13. The system of claim 12, wherein the charged particle is a biomolecule.

14. A method of trapping a charged particle in a trapping volume comprising:
(a) positioning a liquid containing a charged particle between at least three confining electrodes;
(b) applying a time-varying periodic voltage bias to the at least three confining electrodes distributed around the trapping volume;
(c) generating a multipole electric potential in the trapping volume, wherein the multipole electric potential is at least a quadrupole; and
(d) trapping the charged particle within the trapping volume.

15. The method of claim 14, wherein the at least three confining electrodes are N confining electrodes positioned around the trapping volume so that the multipole electric potential in the trapping volume is orthogonal to a longitudinal axis of the trapping volume, wherein N is an even whole number of four or greater.

16. The method of claim 15, wherein the N confining electrodes are coplanar in a plane orthogonal to the longitudinal axis of the trapping volume.

17. The method of claim 14, further comprising flowing the liquid containing the charged particle through a microfluidic channel.

18. The method of claim 14, wherein the liquid containing the charged particle is an electrolytic solution.

19. The method of claim 14, further comprising measuring a property of the charged particle.

* * * * *

UNITED STATES PATENT AND TRADEMARK OFFICE
CERTIFICATE OF CORRECTION

PATENT NO. : 8,294,092 B2  
APPLICATION NO. : 12/730226  
DATED : October 23, 2012  
INVENTOR(S) : Reed et al.

It is certified that error appears in the above-identified patent and that said Letters Patent is hereby corrected as shown below:

In the specification, replace the following paragraph beginning at col. 1, line 10

"This invention was made with government support under Contract Number R21 HG003578 by the NIH National Human Genome Research Institute, R21 HG004764 by the NIH National Human Genome Research Institute, DE-AC05-00ER22725 by the U.S. Department of Energy, and DE-AC02-05CH11231 by the U.S. Department of Energy. The U.S. government has certain rights in this invention."

with:

--This invention was made with government support under HG004764 and HG003578 awarded by National Institutes of Health and DE-AC02-05CH11231 and DE-AC05-00ER22725 awarded by Department of Energy. The government has certain rights in the invention.--

Signed and Sealed this  
Twenty-second Day of January, 2013

David J. Kappos  
*Director of the United States Patent and Trademark Office*